United States Patent
Hamida

(10) Patent No.: US 11,491,197 B2
(45) Date of Patent: Nov. 8, 2022

(54) MULTIPLE VIRAL ANTIGEN COVID VACCINE AND THERAPEUTIC

(71) Applicant: Heba Hamida, Kingston, MA (US)

(72) Inventor: Heba Hamida, Kingston, MA (US)

(73) Assignee: Heba Hamida, Kingston, MA (US)

( * ) Notice: Subject to any disclaimer, the term of this patent is extended or adjusted under 35 U.S.C. 154(b) by 0 days.

(21) Appl. No.: 17/497,295

(22) Filed: Oct. 8, 2021

(65) Prior Publication Data

US 2022/0110987 A1    Apr. 14, 2022

Related U.S. Application Data

(60) Provisional application No. 63/112,669, filed on Nov. 12, 2020, provisional application No. 63/089,072, filed on Oct. 8, 2020.

(51) Int. Cl.
| | | |
|---|---|---|
| A61K 35/76 | (2015.01) | |
| A61K 45/06 | (2006.01) | |
| A61K 39/295 | (2006.01) | |
| A61P 31/12 | (2006.01) | |

(52) U.S. Cl.
CPC .............. *A61K 35/76* (2013.01); *A61K 45/06* (2013.01); *A61P 31/12* (2018.01); *A61K 2121/00* (2013.01); *A61K 2300/00* (2013.01)

(58) Field of Classification Search
CPC ........................... A61K 35/76; A61K 2121/00
See application file for complete search history.

(56) References Cited

U.S. PATENT DOCUMENTS

2015/0273035 A1    10/2015    Feroldi et al.

OTHER PUBLICATIONS

Iftikhar, heathline, https://www.healthline.com/health/coronavirus-prevention; Jun. 4, 2020 (Year: 2020).*
Mayo Clinic, https://www.mayoclinic.org/diseases-conditions/coronavirus/in-depth/treating-covid-19-at-home/art-20483273, accessed on Feb. 8, 2022 (Year: 2022).*
Mahnam et al., Journal of Molecular Graphics and Modelling, 2021; 107:107952 (Year: 2021).*
Soodejani et al., Int J Mol Epidemiol Genet 2021;12(3):35-39 (Year: 2021).*
Diamond, Michael S., and Theodore C. Pierson. "The challenges of vaccine development against a new virus during a pandemic." Cell Host & Microbe 27.5 (2020): 699-703.
Yanuck, S. F., et al. "Evidence supporting a phased immuno-physiological approach to COVID-19 from prevention through recovery." Integrative Medicine: A Clinician's Journal 19.Suppl 1 (2020): 8.
Ma, Shu-Juan, Xing Li, and Yi-Quan Xiong. "Combination measles-mumps-rubella-varicella vaccine in healthy children: a systematic review and meta-analysis of immunogenicity and safety." Medicine 94.44 (2015).
Ahmadi, Shirin, et al. "Scorpion venom: detriments and benefits." Biomedicines 8.5 (2020): 118.
Sifi, Amina, Sonia Adi-Bessalem, and Fatima Laraba-Djebari. "Development of a new approach of immunotherapy against scorpion envenoming: Avian IgYs an alternative to equine IgGs." International immunopharmacology 61(2018): 256-265.
Zheng, Hong-Yi, et al. "Elevated exhaustion levels and reduced functional diversity of T cells in peripheral blood may predict severe progression in COVID-19 patients." Cellular & molecular immunology 17.5 (2020): 541-543.
Qin, Chuan, et al. "Dysregulation of immune response in patients with coronavirus 2019 (COVID-19) in Wuhan, China." Clinical infectious diseases 71.15 (2020): 762-768.
Wang, Dawei, et al. "Clinical characteristics of 138 hospitalized patients with 2019 novel coronavirus-infected pneumonia in Wuhan, China." Jama 323.11 (2020): 1061-1069.
Schmidt, Megan E., and Steven M. Varga. "The CD8 T cell response to respiratory virus infections." Frontiers in immunology 9 (2018): 678.
Vivier, Eric, et al. "Functions of natural killer cells." Nature immunology 9.5 (2008): 503-510.
Henderson LA, Canna SW, Schulert GS, Volpi S, Lee PY, Kernan KF, Caricchio R, Mahmud S, Hazen MM, Halyabar O, Hoyt KJ, Han J, Grom AA, Gattorno M, Ravelli A, De Benedetti F, Behrens EM, Cron RQ, Nigrovic PA. On the Alert for Cytokine Storm: Immunopathology in COVID-19. Arthritis Rheumatol. Jul. 2020;72(7):1059-1063. doi 10.1002/art.41285. Epub May 10, 2020. PMID: 32293098; PMCID: PMC7262347.
Mehtap, McAuley DF, Brown M, Sanchez E, Tattersall RS, Manson JJ; HLH Across Speciality Collaboration, UK. COVID-19: consider cytokine storm syndromes and immunosuppression. Lancet. Mar. 28, 2020;395(10229):1033-1034. doi: 10.1016/S0140-6736(20)30628-0. Epub Mar. 16, 2020. PMID: 32192578; PMCID: PMC7270045.

* cited by examiner

*Primary Examiner* — Gary B Nickol
*Assistant Examiner* — Lakia J Jackson-Tongue
(74) *Attorney, Agent, or Firm* — Tarolli, Sundheim, Covell & Tummino LLP

(57) ABSTRACT

A composition for treating or preventing COVID-19 infection is described. The composition includes attenuated Measles virus particles; attenuated Mumps virus particles; attenuated Rubella II virus particles; scorpion antivenom; and a pharmaceutically acceptable carrier. The composition can be used in a method of treating COVID-19 infection in a subject, and can also be used in a method of vaccinating a subject to decrease the risk or severity of infection by COVID-19.

5 Claims, 6 Drawing Sheets

MULTIPLE VIRAL ANTIGEN COVID VACCINE AND THERAPEUTIC

CROSS-REFERENCE TO RELATED APPLICATIONS

This application claims priority from U.S. Provisional Application Ser. No. 63/089,072, filed Oct. 8, 2020, and U.S. Provisional Application Ser. No. 63/112,669, filed Nov. 12, 2020, both of which are incorporated herein by reference.

BACKGROUND

Coronaviruses are enveloped viruses with a positive-sense single-stranded RNA genome and a helical symmetry. Coronaviruses primarily infect the upper respiratory or gastrointestinal tract of mammals and birds. Five to six different currently known strains of coronaviruses infect humans. SARS-CoV which causes severe acute respiratory syndrome (SARS), has a unique pathogenesis because it causes both upper and lower respiratory tract infections and can also cause gastroenteritis. Middle East respiratory syndrome coronavirus (MERS-CoV) also causes a lower respiratory tract infection in humans.

In November 2002, SARS or severe acute respiratory syndrome was first noted in Guangdong province, China. In February 2003, another outbreak of SARS occurred in Hanoi, Vietnam and was reported to the WHO. It was then on Mar. 10, 2003 that the China SARS of November 2002 and the Hanoi, Vietnam SARS of early 2003 officially became identified as SARS-CoV-1. The Middle East respiratory syndrome coronavirus (MERS-CoV) was subsequently discovered in June 2012. These two earlier coronavirus infections are viewed as primarily local epidemics compared to the 2019 SARS-CoV-2 pandemic.

Clinical samples from patients with pneumonia in Wuhan, China, SARS-CoV-2 was detected in December 2019. Following an initial report in Wuhan, China in December 2019, the World Health Organization (WHO) declared COVID-19 a pandemic on Mar. 11, 2020. COVID-19 has infected over 170 million people and killed 3.5 million people worldwide to date. Coronavirus disease-2019 is the name given to the disease caused by SARS-CoV-2 (COVID-19). SARS-CoV-2 is an extremely infectious and a large proportion of the population is vulnerable to this viral infection. COVID-19 has a broad clinical spectrum of diseases, including fever, dry cough, fatigue, shortness of breath, sore throat, and headache, but the disease can also be asymptomatic, be accompanied by severe pneumonia and progressive dyspnea, or even result in death.

COVID-19 can affect the upper respiratory tract (sinuses, nose, and throat) and the lower respiratory tract (windpipe and lungs). The lungs are the organs most affected by COVID-19 because the virus accesses host cells via the enzyme angiotensin-converting enzyme 2 (ACE2), which is most abundant in type II alveolar cells of the lungs. The virus uses a special surface glycoprotein called a "spike" (peplomer) to connect to ACE2 and enter the host cell, although additional cell surface receptors for COVID-19 entry into cells are also present.

The immune response to SARS-CoV-2 utilizes all the various components of the immune system that fight viral infections in order to eradicate them and recover from infection. Nevertheless, this increased immune response can also lead to a more severe and deadly course of the disease. Along with the vaccines that have been developed and used to date, several therapeutic methods are also being examined to prevent illness. It is believed that it is important at this stage of the COVID-19 pandemic to redesign or improve existing natural and/or pharmaceutical treatments to deal with the virus threat. Natural and herbal remedies have long been used to treat acute respiratory infections and usually demonstrate acceptable toxicity.

Both vaccines and drugs for treating COVID-19 are under development. Previous work to develop a vaccine against the coronavirus diseases SARS and MERS established knowledge about the structure and function of coronaviruses, which accelerated of various technology platforms for a COVID-19 vaccine. Diamond M S, Pierson T C, Cell Host and Microbe. 27 (5): 699-703 (2020). As of the present there are over 300 vaccine candidates in development. Drugs for treating COVID-19 include a number of repurposed antiviral drugs, as well as vasodilators, corticosteroids, immune therapies, lipoic acid, bevacizumab, and recombinant angiotensin-converting enzyme 2. However, neither a safe and effective drug or vaccine has yet been identified. Accordingly, there remains a need for drugs and vaccines that can be used to treat or prevent COVID-19 infection.

SUMMARY

The present invention provides a non-drug, dual purpose vaccine in that effectively vaccinates uninfected patients and both inhibits (e.g., eradicates) COVID-19 and also vaccinates patients actively infected with COVID-19. Once given, the COVID vaccine (i.e., CO-VAX) is believed to rapidly stimulate and potentially promote health to key elements of both the Innate Immune System (IIS) & the Adaptive Immune System (AIS) leading to the desired favorable effects. While not intending to be bound by theory, Applicants have investigated the role of the AIS and IIS in the effectiveness of CO-VAX.

The IIS is composed of Natural Killer Cells, Neutrophils, Monocytes, Macrophages, Dendritic cells, along with set of complement proteins, and a combination of various cytokines (e.g., interferons, interleukins, and growth factors). Stimulation of the innate immune system is important for the successful eradication of COVID-19 in infected subjects, and for the simultaneous or separate "vaccination" of both infected or non-infected subjects.

While the present invention vaccinates and prepared uninfected subjects to successfully resist subsequent COVID-19 exposure, it is also believed to provide timely successful activation of the IIS to mount a successful attack against COVID-19 in an individual who is already infected. The IIS represents the first-line defense against COVID-19. A delayed type I interferon response (Yanuck, S F, Integrative Medicine, 19: 8-35 (2020)) along with diminished production of type II interferon, specifically interferon-γ (IFN-γ) by natural killer (NK) cells and activated T cells increases the risk of entering a more serious phase of COVID-19 infection. The present invention is believed to rapidly enable the innate immune system's and the adaptive immune systems ability, in an infected individual, to produce timely secretion of type I interferons and type II interferon or IFN-γ.

IFN-γ is primarily secreted by NK cells in the IIS and by activated T cells in the AIS. They promote macrophage activation, mediate antiviral and antibacterial immunity, enhance antigen presentation, orchestrate activation of the innate immune system, coordinate lymphocyte-endothelium interaction, and regulate Th1/Th2 balance. The IFN-γ component of the immune response plays an essential role in combating infectious and non-infectious diseases.

Type III interferons are another important group of antiviral cytokines. Their function is similar to that of type I interferons, but is less intense and serves mostly as a first-line defense against viruses in the epithelium. The type I and type III interferon families consist of cytokines that are rapidly induced during viral infection and confer antiviral protection on target cells. They play an important role in the innate immune response, and the transition to an effective adaptive immune response. The present invention helps restore the ability of a patient to produce interferons, and to do so on a timely basis.

The AIS is composed of cell mediated immunity CD4+T helper cells, CD4+ cytotoxic T cells, and CD8+ cytotoxic T cells along with cytokines. Other types of T cells include T regulatory cells and T follicular cells. B cells are another type of immune cells that uniquely produce antibodies. T helper cells help B cells become plasma cells which provide humoral or "antibody mediated' immunity.

Until recently, it was felt that an individual's level of "neutralizing antibodies" acquired from a prior COVID19 infection or from "any effective vaccine" represented the main source that would protect individuals from new or recurrent COVID19 infections. However, it appears that the presence of IgG antibodies directed against elements of COVID19 represent evidence of prior exposure to COVID19 but are not necessarily the most important "biomarker of protection." Measurements of NK cell immunity. and T cell immunity along with the presence of the still undetermined most protective cytokine profile would likely better define COVID19 protection.

The vaccine of the present invention provides easy of administration, few side effects, biological stability, and low cost per dose. Additionally, CO-VAX has the key features required for effective vaccines, such as being safe so the vaccine does not itself cause death or illness, and is protective against illness resulting from exposure to live pathogens such as viruses or bacteria.

CO-VAX is believed to promote an individual's ability to have a "ready to fight" innate immune system by forming fresh memory NK cells and promoting a "ready to fight" AIS by inducing protective memory T cells against intracellular COVID-19. While CO-VAX does not contain an attenuated form of the coronavirus, bur rather uses a modified re-purposed vaccine (i.e., the Measles, Mumps, Rubella (MMR) vaccine) that results in a re-awakening of an individual's immune system, particularly one that has been previously exposed to the MMR vaccine. Antigenic stimulation by the MMR vaccine results in memory NK cells and memory T cells that induce an immune defense against COVID-19. The integrative cooperation between the IIS and AIS is believed to essentially minimize the need for the production of antibodies by B cells of the AIS.

CO-VAX represents a unique non-drug patent-protected product that causes the rapid mobilization of key elements of both the innate and the adaptive immune system with associated cytokine formation and release. There has been limited clinical experience in Europe that support both the therapeutic and preventive effects, strongly suggesting the safe efficacy of CO-VAX. Is should also be noted that clinically dramatic effects of rapid clinical healing were often seen when CO-VAX was given to infected patients.

The occurrence of side effects linked to CO-VAX have been minimal and have consisted of infrequent (<15%) brief local reactions at the site of injection and the occurrence of a headache (<10%) occurring within the first 3 days and lasting for 2-3 days without any other neurological symptoms, abnormal physical findings or subsequent recurrent symptoms.

DETAILED DESCRIPTION

Figure 1A:
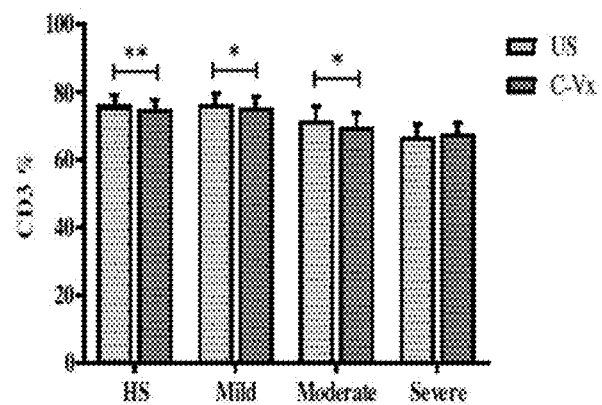
FIGS. 1A-1C provides graphs showing the alterations in the frequencies of T and NK cells in response to the stimulation with C-Vx. (A) CD3+ total T cells, (B) CD3$^-$CD16$^+$CD56$^+$ NK cells, (C) CD4$^+$ (on left) and CD8$^+$ (on right) T cells of COVID-19 patients and healthy subjects.

The present invention provides a composition for treating or preventing COVID-19 infection. The composition includes attenuated Measles virus particles; attenuated Mumps virus particles; attenuated Rubella II virus particles; scorpion antivenom; and a pharmaceutically acceptable carrier. The composition can be used in a method of treating COVID-19 infection in a subject, and can also be used in a method of vaccinating a subject to decrease the risk or severity of infection by COVID-19.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, and other references mentioned herein are incorporated by reference in their entirety.

Definitions

As used in the description of the invention and the appended claims, the singular forms "a," "an," and "the" are intended to include the plural forms as well, unless the context clearly indicates otherwise. In addition, the recitations of numerical ranges by endpoints include all numbers subsumed within that range (e.g., 1 to 5 includes 1, 1.5, 2, 2.75, 3, 3.80, 4, 5, etc.).

As used herein, the term "polypeptide" is intended to encompass a singular "polypeptide" as well as plural "polypeptides," and comprises any chain or chains of two or more amino acids. Thus, as used herein, terms including, but not limited to "peptide," "dipeptide," "tripeptide," "protein," "amino acid chain," or any other term used to refer to a chain or chains of two or more amino acids, are included in the definition of a "polypeptide," and the term "polypeptide" may be used instead of, or interchangeably with any of these terms. The term further includes polypeptides which have undergone post-translational modifications, for example, glycosylation, acetylation, phosphorylation, amidation, derivatization by known protecting/blocking groups, proteolytic cleavage, or modification by non-naturally occurring amino acids.

The term "antigen" as used herein refer to a portion or portions of molecules which are capable of inducing a specific immune response in a subject alone or in combination with an adjuvant. The term "epitope," as used herein, refers to a portion of a polypeptide having antigenic or immunogenic activity in an animal, for example a mammal, for example, a human.

The term "immune response", as used herein, refers to an alteration in the reactivity of the immune system of an animal in response to an antigen or antigenic material and may involve antibody production, induction of cell-mediated immunity, complement activation, development of immunological tolerance, or a combination thereof.

The term "passive immunity" refers to the immunity to an antigen developed by a host animal, the host animal being given antibodies produced by another animal, rather than producing its own antibodies to the antigen. The term "active immunity" refers to the production of an antibody by a host animal as a result of the presence of the target antigen.

The term "immunoprotection" as used herein, mean an immune response that is directed against one or more antigen so as to protect against disease and/or infection by a pathogen in a vaccinated animal. For purposes of the present invention, protection against disease includes not only the absolute prevention of the disease, but also any detectable reduction in the degree or rate of disease, or any detectable reduction in the severity of the disease or any symptom in the vaccinated animal as compared to an unvaccinated infected or diseased animal, which is also referred to as inhibition of the disease. Immunoprotection can be the result of one or more mechanisms, including humoral and/or cellular immunity.

The term "vaccine", as used herein, refers to a preparation that is used to establish immunity to a disease, thereby protecting a body from a disease, or reducing the chances of a body becoming affected by the disease. Vaccines can be preventative against the effects of a future infection or therapeutic (intended to reduce the severity of an infection or a disease, typically by assisting the immune system in fighting the infection or disease). In certain embodiments of the invention, a vaccine is a preparation that is used to establish immunity to a disease in the offspring of the individual to which the vaccine is delivered.

The term "pathogenicity" is used herein according to its normal meaning to refer to the potential of the virus to cause disease in a subject. Typically the pathogenicity of a coronavirus is determined by assaying disease associated symptoms, for example wheezing, snicking and reduction in tracheal ciliary activity.

"Treating", as used herein, means ameliorating the effects of, or delaying, halting or reversing the progress of a disease or disorder. The word encompasses reducing the severity of a symptom of a disease or disorder and/or the frequency of a symptom of a disease or disorder.

A "subject", as used therein, can be a human or non-human animal. Non-human animals include, for example, livestock and pets, such as ovine, bovine, porcine, canine, feline and murine mammals, as well as reptiles, birds and fish. Preferably, the subject is human.

The language "effective amount" or "therapeutically effective amount" refers to a nontoxic but sufficient amount of the composition used in the practice of the invention that is effective to provide effective vaccination or treatment in a subject. That result can be reduction and/or alleviation of the signs, symptoms, or causes of a disease or disorder, or any other desired alteration of a biological system. An appropriate effective amount for a subject may be determined by one of ordinary skill in the art using routine experimentation.

A "prophylactic" or "preventive" treatment is a treatment administered to a subject who does not exhibit signs of a disease or disorder, or exhibits only early signs of the disease or disorder, for the purpose of decreasing the risk of developing pathology associated with the disease or disorder. Use of a vaccine in a preventive treatment provides immunoprotection.

Compositions for Treating or Preventing COVID-19 Infection

In one aspect, the present invention provides a composition for treating or preventing COVID-19 infection. The composition includes attenuated Measles virus particles; attenuated Mumps virus particles; attenuated Rubella II virus particles; scorpion antivenom; and a pharmaceutically acceptable carrier.

Measles, mumps and rubella are diseases that may be prevented by a single administration of a live attenuated measles, mumps and rubella combination vaccine, generically designated under the term MMR vaccine. The combination of a live attenuated measles virus, a live attenuated mumps virus and a live attenuated rubella virus is also referred to as the MMR vaccine. For a description of a live attenuated measles-mumps-rubella (MMR) vaccine, see US Patent Publication No. 20150273035. Examples of useful measles virus strains include the attenuated Enders-Edmonston, Edmonston-Zagreb and Schwarz strains and any attenuated strain derived therefrom. Examples of useful mumps virus strains include the attenuated Jeryl Lynn, Urabe AM 9, and Rubini strains and any attenuated strain derived therefrom, such as the RIT 4385 strain which is derived from the Jeryl Lynn strain. Examples of rubella virus strains include the Wistar RA 27/3 and Wistar RA 27/3M strains. In addition to the attenuated measles, mumps and rubella strains, the MMR vaccine may also comprise an attenuated varicella-zoster strain such as the Oka/Merck or Oka strain. In that case, the MMR vaccine may be designated the "MMRV vaccine".

Examples of commercially available MMR vaccines include the M-M-® II vaccine (Merck & Co, Whitehouse Station, N.J. USA), the Triviraten Berna® vaccine (also referred to as the Berna-MMR, Berna Biotech, Basel, Switzerland), the Priorix™ vaccine (Glaxo SmithKline Biologics, Rixensart, Belgium), and the Trimovax® vaccine (Sanofi Pasteur SA, Lyon, France).

The Measles, Mumps, and Rubella II virus particles are all attenuated. The term "attenuated" as used herein refers to a virus that exhibits said reduced pathogenicity and may be classified as non-virulent. A live, attenuated virus is a weakened replicating virus still capable of stimulating an immune response and producing immunity but not causing the actual illness. The term "reduced pathogenicity" is used to describe that the level of pathogenicity of the virus particles is decreased, lessened or diminished compared to corresponding wild-type virus particles.

Viruses may be attenuated via passage of the virus through a foreign host. Examples of foreign hosts include tissue culture, embryonated eggs, and live animals. To achieve attenuation, the initial virus population is applied to a foreign host. Through natural genetic variability or induced mutation, a small percent of the viral particles should have the capacity to infect the new host. These strains will continue to evolve within the new host and the virus will gradually lose its efficacy in the original due to lack of selection pressure. This process is known as "passage" in which the virus becomes so well adapted to the foreign host that it is no longer harmful to the vaccinated subject. This makes it easier for the host's immune system to eliminate the agent and create the immunological memory cells which will likely protect the patient if they are infected with a similar version of the virus in "the wild".

In certain embodiments, the virus particles are attenuated by tissue culture passage. This method has been used as a live oral vaccine for wildlife in Europe for many years. attenuated by approximately 120 passages in embryonated chicken eggs.

In some embodiments, the amount of virus particles (i.e., measles, mumps, and rubella virus particles) is lower than the amount provided by a conventional MMR II vaccine. The amount of virus particles present in a standard MMR II vaccine are well-known to those skilled in the art. See Ma et al., Medicine (Baltimore). 2015 November; 94(44):e1721. In some embodiments, the amount of virus particles present in the composition is about 90%, about 80%, about 70%, about 60%, about 50%, about 40%, about 30%, about 20%, or about 10% of the amount of virus particles present in a standard MMRII vaccine dose.

In some embodiments, the attenuated Measles virus particles provide a CCID50 from 200 to 300, the attenuated Mumps virus particles a CCID50 from 5500 to 6000 CCID50, and the attenuated Rubella II virus particles provide a CCID50 from 200 to 300.

The composition also includes scorpion antivenom. The composition of conventional scorpion antivenoms are well-known to those skilled in the art. See Ahmadi et al., Biomedicines. 2020 May 12; 8(5):118. Conventional plasma-derived antivenoms are produced by the purification (and digestion) of polyclonal immunoglobulin G (IgG) molecules harvested from the plasma of hyperimmunized animals, such as horses or sheep. However, strategies involving avian egg-yolk-derived immunoglobulin Ys (IgYs) have also been developed. Sifi et al., Int. Immunopharmacol. 2018, 61, 256-265. In some embodiments, the scorpion antivenom is γ-scorpion antivenom.

In some embodiments, the amount of scorpion antivenom is lower than the amount present in a conventional scorpion antivenom composition. In some embodiments, the amount of virus particles present in the composition is about 50%, about 40%, about 30%, about 20%, about 15%, about 10% or about 5% of the amount of scorpion antivenom present in a standard scorpion antivenom dose. Preferably, the amount of scorpion antivenom is about 5% of the standard scorpion antivenom dose. In further embodiments, the amount of scorpion antivenom provides an LD50 of from 1 to 10, from 2 to 8, or from 3 to 5.

In some embodiments, the vaccine composition includes one or more nutrients. These nutrients can improve the effect, in some cases synergistically, of the vaccine composition. While not intending to be bound by theory, the nutrients provide support for the immune cells being affected by the vaccine composition. In some embodiments, the nutrients are selected from the group consisting of glutathione, zinc, and vitamin D.

Zinc plays an important role in most immune cells, and has well-known antiviral properties, including blocking the replication of RNA viruses in cell culture and lowering the harmful effects of interleukin-6. Increasing the intracellular $Zn^{2+}$ concentration with zinc ionophores like pyrithone (PT) can efficiently impair replication of a variety of RNA viruses, including polio virus and influenza virus. It has been shown that the combination of $Zn^{2+}$ and PT at low concentrations (2 μM $Zn^{2+}$ and 2 μM PT) inhibits the replication of SARS-coronavirus (SARS-COV) and equine arteritis virus (EAV) in cell culture Low levels of Vitamin D impair immune function, promote inflammation, and impair the cytocidal effect of macrophages. There has been a hypothesis proposed that there is a potential association between mean levels of Vitamin D in various countries with cases and mortality caused by COVID-19. The mean levels of Vitamin D for 20 European countries and morbidity and mortality caused by COVID-19 were acquired. Negative correlations between mean levels of Vitamin D (average 56 mmol/L. STEDV 10.61) in each country and in the number of COVID-19 cases/1 M (mean 295.95, STDEV 298.7, and mortality/1M (mean 5.96 STDEV 15.13) were observed. Vitamin D levels are severely low in the aging population, especially in Spain, Italy and Switzerland. This is also the most vulnerable group of the population in relation to COVI-19.

Glutathione is an intracellular reducing agent that helps maintain the redox potential of the cell and is important for immune function. Glutathione has been reported to block the replication of HIV, HSV-1, and influenza virus, whereas cells treated with BSO exhibit increased replication of Sendai virus. Since the antiviral effect of glutathione is non-specific, there is reason to believe that glutathione is also active against SARS-COV-2. Research has shown that active glutathione (GSH) primes white cells such as natural killer (NK) and T-cells, the body's front-line infection fighters. GSH-enhanced T cells are able to produce more infection-fighting substances, controlling both bacterial and viral infections.

Methods of Treating COVID-19 Infection

Another aspect of the invention provides a method of treating, preventing, or inhibiting COVID-19 infection in a subject. The method includes administering a therapeutically effective amount of the vaccine composition described herein to the subject. The vaccine composition includes attenuated Measles virus particles; attenuated Mumps virus particles; attenuated Rubella II virus particles; scorpion antivenom; and a pharmaceutically acceptable carrier. In some embodiments, the method is specifically directed to treating COVID-19 infection in a subject. While the therapeutic composition is frequently referred to herein as a "vaccine composition," that is not intended to limit the use of the composition to vaccination.

In some embodiments, the method is used to treat or prevent COVID-19 infection in a subject in need of therapeutic or preventive immunity. As used herein, "a subject in need of therapeutic and/or preventive immunity" refers to a subject who has, or has an increased risk for developing COVID-19 infection, or an increased susceptibility to COVID-19 infection. For example, a subject may have increased risk for developing COVID-19 infection if they are known to have been exposed to COVID-19, or may have an increased susceptibility to COVID-19 infection if they are diabetic or have one or more known risk factors for COVID-19 infection, such as increased age, male gender, or obesity.

The method of treatment or prevention of COVID-19 infection can use any of the vaccine compositions described herein. In some embodiments, the therapeutically effective amount is a lower dose than what is provided when administering a conventional MMR II vaccine. In further embodiments, the composition includes attenuated Measles virus particles that provide a CCID50 from 200 to 300, attenuated Mumps virus particles that provide a CCID50 from 5500 to 6000 CCID50, and attenuated Rubella II virus particles that provide a CCID50 from 200 to 300. In yet further embodiments, the composition further comprises one or more nutrients selected from the group consisting of glutathione, zinc, and vitamin D.

In some embodiments, the composition is administered to the subject by injection using a suitable injectable composition. In further embodiments, only a single dose is administered to the subject. The dosage administered is typically smaller than the dosage used for a standard MMR vaccination, based on the fact that treatment typically involves administering a smaller amount of the MMR virus particles than is used for MMR vaccination.

COVID-19 Vaccination

Another aspect of the method provides a method of vaccinating a subject to decrease the risk or severity of infection by COVID-19. The method includes administering an effective dose of the vaccine composition to the subject. The vaccine composition includes attenuated Measles virus particles; attenuated Mumps virus particles; attenuated Rubella II virus particles; scorpion antivenom; and a pharmaceutically acceptable carrier.

The vaccine can induce a humoral immune response in the subject administered the vaccine. The humoral immune response induced by the vaccine can include an increased level of neutralizing antibodies associated with the subject administered the vaccine as compared to a subject who was not administered the vaccine. The humoral immune response can be induced in the subject administered the vaccine by about 1.5-fold to about 16-fold, about 2-fold to about 12-fold, or about 3-fold to about 10-fold, or about 10-fold to about 15-fold, compared to the response of a subject who was not administered the vaccine. In some embodiments of the invention, an effective amount of a vaccine composition of the invention produces an elevation of antibody titer to at least two or three times the antibody titer prior to administration.

The vaccine can induce a cellular immune response in the subject administered the vaccine. The induced cellular immune response can include eliciting a CD8+ T cell response. The elicited CD8+ T cell response can be reactive with the MERS-CoV antigen. The elicited CD8+ T cell response can be polyfunctional. The induced cellular immune response can include eliciting a CD8+ T cell response, in which the CD8+ T cells produce interferon-gamma (IFN-$\gamma$), tumor necrosis factor alpha (TNF-$\alpha$), interleukin-2 (IL-2), or a combination of IFN-$\gamma$ and TNF-$\alpha$. The induced cellular immune response can include an increased CD8+ T cell response associated with the subject administered the vaccine as compared to a subject who was not administered with the vaccine. The CD8+ T cell response associated with the subject administered the vaccine can be increased by about 2-fold to about 30-fold, about 3-fold to about 25-fold, or about 4-fold to about 20-fold as compared to subjects who were not administered with the vaccine.

The method includes vaccinating a subject to decrease the risk or severity of infection by COVID-19. Decreasing the risk of infection refers to decreasing the chance that a subject will develop a COVID-19 infection. Vaccination with the composition can decrease the chance that a subject will develop a COVID-19 infection by at least 20%, at least 30%, at least 40%, at least 50%, at least 60%, at least 70%, at least 80%, at least 90%, or at least 95% compared with the typical outcome when a vaccine is not administered to the subject.

Vaccination can also decrease the severity of infection should the subject nonetheless develop a COVID-19 infection. Decreasing the severity of infection can result in a decreased number of symptoms of COVID-19 occurring in the subject, or a decrease in the severity of the symptoms that do occur. Common COVID-19 symptoms include fever, dry cough, and tiredness. More severe COVID-19 symptoms include difficulty breathing or shortness of breath, chest pain or pressure, and loss of speech of movement. Less common symptoms include aches and pains, sore throat, diarrhea, conjunctivitis, headache, loss of taste or smell, and a rash on skin, or discoloration of fingers or toes.

The method of vaccination can use any of the vaccine compositions described herein. In some embodiments, the effective amount is a lower dose than what is provided when administering a conventional MMR II vaccine. In further embodiments, the composition includes attenuated Measles virus particles that provide a CCID50 from 200 to 300, attenuated Mumps virus particles that provide a CCID50 from 5500 to 6000 CCID50, and attenuated Rubella II virus particles that provide a CCID50 from 200 to 300. In yet further embodiments, the composition further comprises one or more nutrients selected from the group consisting of glutathione, zinc, and vitamin D.

In some embodiments, the vaccine composition is administered to the subject by injection using a suitable injectable composition. In further embodiments, only a single dose is administered to the subject. The dosage administered is typically smaller than the dosage used for a standard MMR vaccination, based on the fact that treatment typically involves administering a smaller amount of the MMR virus particles than is used for MMR vaccination.

In some embodiments, the vaccine composition is administered with an adjuvant. As used herein, an "adjuvant" refers to any substance which, when administered with or before the vaccine composition, aids the vaccine composition in its stimulation of an immune response. One or more of the above described vaccine components may be admixed or adsorbed with a conventional adjuvant. Adjuvants may, in certain embodiments, enhance production of antibodies against COVID-19. Examples of suitable adjuvants include, but are not limited to, various oil formulations and/or emulsions such as stearyl tyrosine (see, for example, U.S. Pat. No. 4,258,029), muramyl dipeptide (also known as MDP, Ac-Mur-L-Ala-D), saponin, aluminum hydroxide, lymphatic cytokine, Freund's adjuvant, cholera toxin (e.g., the Cholera toxin B subunit), heat labile enterotoxin (KT) from *E. coli*, Emulsomes (Pharoms, LTF., Rehovot, Israel), etc.

Formulation and Administration

The vaccine compositions described herein include a pharmaceutically acceptable carrier, which constitutes one or more accessory ingredients. The term "pharmaceutically acceptable", when used in reference to a carrier, is meant that the carrier, diluent or excipient must be compatible with the other ingredients of the formulation and not deleterious to the recipient thereof.

Vaccines may be formulated for any of a variety of routes of administration as discussed further below. For example, vaccines may be formulated as a spray for intranasal inhalation, nose drops, swabs for tonsils, etc. Vaccines may be formulated for oral delivery in the form of capsules, tablets, gels, thin films, liquid suspensions and/or elixirs, etc. Optionally, the vaccine compositions may optionally contain adjuvants, preservatives, chemical stabilizers, as well as other conventionally employed vaccine additives. Typically, stabilizers, adjuvants, and preservatives are optimized to determine the best formulation for efficacy in the target human or animal. Suitable exemplary preservatives include chlorobutanol, potassium sorbate, sorbic acid, sulfur dioxide, propyl gallate, the parabens, ethyl vanillin, glycerin, phenol, and parachlorophenol.

A variety of pharmaceutically acceptable protein carriers, and/or components suitable for administration therewith may be selected by one of skill in the art. For example, pharmaceutical carriers include, without limitation, sterile saline, lactose, sucrose, calcium phosphate, gelatin, dextran, agar, pectin, peanut oil, olive oil, sesame oil, and water. Additionally, the carrier or diluent may include a time delay material, such as glycerol monostearate or glycerol distearate alone or with a wax. In addition, slow release polymer formulations can be used. Liposomes or liposomal-like vehicles may also be employed.

Optionally, vaccine compositions may also contain conventional pharmaceutical ingredients, such as preservatives, or chemical stabilizers. Suitable ingredients which may be used in a therapeutic composition in conjunction with the antibodies include, for example, casamino acids, sucrose, gelatin, phenol red, N-Z amine, monopotassium diphosphate, lactose, lactalbumin hydrolysate, and dried milk.

The vaccine composition may be administered 1-3 times per day over a 1 day to 12 week period. However, suitable dosage adjustments for protein or nucleic acid containing compositions may be made by the attending physician or veterinarian depending upon the age, sex, weight and general health of the human or animal patient. Routes of administration also include subcutaneous, intradermal, and intramuscular. Preferably, such a composition is administered parenterally, preferably intramuscularly or subcutaneously. However, it may also be formulated to be administered by any other suitable route, including orally or topically. The selection of the route of delivery and dosage of such therapeutic compositions is within the skill of the art.

In a preferred embodiment, the pharmaceutically acceptable carrier is a carrier suitable for administration by injection. For example, a one-time injection of the vaccine composition is given subcutaneously via a very small needle. It is composed of a total volume of 0.5 ml, which is delivered by two very small separate injections of 0.25 ml in the lateral buttock and 0.25 ml in the upper arm-shoulder area. However, the vaccine can further induce an immune response when administered to different tissues such as the muscle or skin. The vaccine can further induce an immune response when administered via electroporation, or injection, or subcutaneously, or intramuscularly.

The vaccine composition is administered in an "effective amount", that is, an amount of antigenic virus particles and scorpion antivenom that is effective in a route of administration to provide a vaccinal benefit, i.e., protective immunity, or in a "therapeutically effective amount," to treat COVID-19 infection in a subject. Suitable amounts of the antigenic virus particles (and scorpion antivenom) can be determined by one of skill in the art based upon the level of immune response desired. In general, however, the vaccine composition contains between 1 ng to 1000 mg antigen, and more preferably, 0.05 μg to 1 mg per ml of antigen. Suitable doses of the vaccine composition of the invention can be readily determined by one of skill in the art. Generally, a suitable dose is between 0.1 to 5 ml of the vaccine composition. Further, depending upon the human patient or the animal species being treated, i.e. its weight, age, and general health, the dosage can also be determined readily by one of skill in the art.

Dosing regimens may comprise a single immunization or multiple immunizations. For example, vaccines may be given as a primary immunization followed by one or more boosters. Boosters may be delivered via the same and/or different route as the primary immunization. Boosters are generally administered after a time period after the primary immunization or the previously administered booster. For example a booster can be given about two weeks or more after a primary immunization, and/or a second booster can be given about two weeks or more after the first boosters. Boosters may be given repeatedly at time periods, for example, about two weeks or greater throughout up through the entirety of a subject's life. Boosters may be spaced, for example, about two weeks, about three weeks, about four weeks, about one month, about two months, about three months, about four months, about five months, about six months, about seven months, about eight months, about nine months, about ten months, about eleven months, about one year, about one and a half years, about two years, about two and a half years, about three years, about three and a half years, about four years, about four and a half years, about five years, or more after a primary immunization or after a previous booster.

The following example is included for purposes of illustration and is not intended to limit the scope of the invention.

EXAMPLE

Example 1: CO-VAX Composition #1

When reconstituted with the sterile diluent provided, each 0.14 mL dose of MEASLES, MUMPS, and RUBELLA II contains:

Active Ingredients:
- Measles virus (>286 CCID50)
- Mumps virus (>5700 CCID50)
- Rubella virus (>286 CCID50)
- Gamma Scorpion (Anti Venom): 0.38 ml
- *Androctonus australis* (>3.85 LD50)
- *Bothus occitanus* (>3.85 LD50)

Inactive Ingredients:
- Sodium Phosphate, Monobasic (0.9 mg)
- Sodium Phosphate, Dibasic (0.6 mg)
- Sodium Bicarbonate (0.14 mg)
- Medium 199 (0.94 mg)
- Minimum Essential Medium, Eagle (0.03 mg)
- Neomycin (7.14 μg)
- Phenol Red (0.97 μg)
- Sorbitol (4.14 mg)
- Potassium Phosphate, Monobasic (5.71 μg)
- Potassium Phosphate, Dibasic (8.57 μg)
- Gelatin (Bovine) Hydrolyzed (4.14 mg)
- Sucrose (0.54 mg)
- Monosodium L-Glutamate
- Water for Injection (5.71 μg)

Nutrient Composition
- Glutathione (Tationil) (69.2 mg)
- Zinc (Zinkorell) (0.12 ml+11.5 mg Zinc from 900 mg Zinc Gluconate)
- Vitamin D (4,050 IU)

Example 2: CO-VAX Composition #2

Each 0.5 mL dose of CO-VAX vial contains:
Active Ingredients (Attenuated Viruses)
  Measles virus (>240 TCID50)
  Mumps virus (>4800 TCID50)
  Rubella virus (>240 TCID50)
Active Ingredients (Anti-Venoms)
  Gamma Scorpion
  *Androctonus australis* (>4.5 LD50)
  *Buthus occitanus* (>4.5 LD50)
Pharmaceutical Carrier Ingredients:
  Sodium Phosphate, Monobasic (0.75 mg)
  Sodium Phosphate, Dibasic (0.53 mg)
  Sodium Bicarbonate (0.12 mg)
  Medium 199 (0.80 mg)
  Minimum Essential Medium, Eagle (0.02 mg)
  Neomycin (6.06 μg)
  Phenol Red (0.82 μg)
  Sorbitol (3.51 mg)
  Potassium Phosphate, Monobasic (4.85 μg)
  Potassium Phosphate, Dibasic (7.27 μg)
  Gelatin (Bovine) Hydrolized (3.51 μg)
  Sucrose (0.46 mg)
  Monosodium L-Glutamate (4.85 μg)
Nutrient Ingredients:
  Vitamin D3 (2272.7 iu)
  Zinc (as Zinc Gluconate) (45.4 μg)
  Glutathione (27.3 mg)

Example 3: The Immunomodulatory Action of C-Vx Substance on Immune System in COVID-19

Initially, the substance of C-Vx was developed and formulated for cancer treatment by Pharma-USA in conjunction with Miracle Labs, Turkey. However, with the emergence of COVID-19 in the globe, the scientific team has made additional improvements to the formula and is presenting C-Vx as a currently active immunostimulant product. The unique and novel new formulation of C-Vx's claims to provide effective concurrent therapy against active COVID-19 infection. The passive immunological component in C-Vx is predicted to rapidly kill the virus, preventing active cellular entry of SARS-CoV-2 both superficially and internally. At this point, the prophylactic use of natural products like C-Vx for the prevention of the disease and for the treatment of infected patients promises to become a helpful therapeutic approach.

After being infected with SARS-CoV-2, the immune system essentially begins a "war" with the pathogen. During this struggle, it is possible that the pathogen may cause the human body's immune cells to die or the pathogen may result in a functional inhibition in a way that significantly affects disease development. Recent studies show that the number of total lymphocytes, CD4+ and CD8+ T cells, and Natural Killer (NK) cells have decreased significantly in serious cases and it has been reported that high levels of exhaustion and decreased functional diversity of peripheral blood T cells can contribute the disease's progression in patients with COVID-19. Zheng et al., Cell Mol Immunol, 17(5):541-543 (2020); Qin C et al., Clin Infect Dis., 71 (15): 762-768 (2020); Wang, D et al., JAMA, 323: Number 11 (2020). $CD8^+$ T and NK cells are recognized to have a critical role in the management of pathogenic infection by mediating cellular immunity and cytotoxic functions as primary cytotoxic lymphocyte. Schmidt et al., Front Immunol, 9:678 (2018); Eric Vivier et al., Nat Immunology, 9(5):503-10 (2008).

Excessive release pro-inflammatory cytokines and chemokines often appears to lead to serious complications of the disease including inflammatory-induced lung injury and pneumonitis, acute respiratory distress syndrome (ARDS), respiratory failure and potentially death. Henderson, Laura A et al., Arthritis Rheumatol, 72(7): 1059-1063 (2020); Mehta et al., Lancet, 395(10229):1033-1034 (2020).

So far, there is no current specific and effective treatment for COVID-19. We currently believe that C-Vx immunotherapies based on immunomodulation can reduce inflammation and inflammatory-related lung damage. C-Vx can be used as an immunostimulant that can rapidly stimulate both innate and adaptive immune arms. Therefore, in order to see within COVID-19 patients, the action of the C-Vx immunomodulatory substance, it would be necessary to better characterize and understand the status and functionality of immune cells.

In this study, we have provided this new approach to the prevention and treatment of COVID-19 disease using C-Vx substance with its immunomodulatory potential. We also address the immunological aspects of this proposed treatment. Treatment possibilities for the global coronavirus pandemic are a much needed and highly currently researched field.

Methods

Study Design and Participants

COVID-19 patients (n=31; 15 male and 16 female) admitted to Istanbul University Faculty of Medicine were enrolled in this study. All patients with SARS-CoV-2 infection, which was confirmed by PCR positivity, were receiving treatment of hydroxychloroquine and azithromycin by the time of sampling. Patients were sub-grouped as mild (n=10), moderate (n=11) and severe (n=10) according to the clinical course (Table 1). The biochemical parameters of patient groups are given in Table 2. Age- and gender-matched healthy donors (n=10; 6 male and 4 female) without any known disease were also included in the study. All donors were unvaccinated against COVID-19 at the time of sampling. An approval of Istanbul Faculty of Medicine, Clinical Research Ethics Committee was obtained in compliance with Helsinki declaration.

TABLE 1

| Demographic characteristics, treatment | | | |
|---|---|---|---|
| | Mild | Moderate | Severe |
| n | 10 | 11 | 10 |
| Gender | 5 males | 5 males | 5 males |
| | 5 females | 6 females | 5 females |
| Age [Median (min-max)] | 45 (21-79) | 54.8 (33-78) | 63.2 (50-73) |

TABLE 1-continued

| Demographic characteristics, treatment | | | |
|---|---|---|---|
| | Mild | Moderate | Severe |
| Treatment | Hydroxychloroquine, azithromycin | Hydroxychloroquine, azithromycin, favipravir | Hydroxychloroquine, azithromycin, favipravir, Tociluzumab |

TABLE 2

| Biochemical Parameters of Patients | | | | |
|---|---|---|---|---|
| | Mild Median (min-max) | Moderate Median (min-max) | Severe Median (min-max) | Reverences Values |
| White Blood Cells ($10^3/\mu L$) | 8.03 (3.9-13.2) | 6.6 (3.4-11) | 10.4 (5-16.6) | 4-10 |
| Lymphocytes ($10^3/\mu L$) | 1.55 (0.6-3.1) | 1.26 (0.5-2.4) | 1.35 (0.2-5.9) | 1.2-3.6 |
| Neutrophils ($10^3/\mu L$) | 5.88 (2.1-11.8) | 4.96 (1.7-10.1) | 7.93 (0.6-15.4) | 1.3-7 |
| Platelets ($10^3/\mu L$) | 276.3 (177-528) | 238.1 (124-364) | 261.9 (123-476) | 160-390 |
| CRP (mg/dL) | 40.1 (0-164) | 58.9 (3-150) | 153.7 (13-528) | 0-5 |
| D-Dimer ($\mu g/L$) | 968.9 (190-3700) | 922.7 (220-1640) | 4370 (380-18450) | 0.0-550 |
| Ferritin (ng/mL) | 192.9 (22-842) | 572.3 (24-1404) | 6068.6 (232-46852) | 13-400 |
| Procalcitonin (ng/mL) | 0.08 (0.01-0.19) | 0.1 (0.01-0.35) | 10.97 (0.07-48.89) | 0-0.5 |

Sample Preparation

Peripheral venous blood samples were collected from patients and healthy donors and peripheral blood mononuclear cells (PBMCs) were isolated from heparinized blood samples by density gradient centrifugation using Ficoll-Paque (Histopaque-1077; Biochrom, Cambridge, UK). Cells washed twice with phosphate-buffered saline (PBS) were suspended in RPMI-1640 medium (Sigma Chem. Co., Germany) and were freshly used in culture assays. Plasma samples separated from heparinized blood of donors were frozen at −200° C. until use in further ELISA and multiplex assays.

Dose Experiments with Different Concentrations of C-Vx

In order to determine the concentration of C-Vx which has no toxic effect on human cells, PBMCs ($1\times10^6$/mL) obtained from one healthy donor were cultured at different concentrations of C-Vx (1/50, 1/100 and 1/250) for 24, 48 and 72 hours. Unstimulated (US) and also phytohemagglutinin (PHA, 2 μg/mL)-stimulated conditions were used as control and cells were maintained in a 37° C. incubator containing 5% $CO_2$. After the cell culture, the apoptotic index was measured by using Annexin V-Apoptosis Detection Kit I (Biolegend, San Jose, Calif., USA). Briefly, harvested cells were stained with Annexin V-FITC and then propidium iodide (PI) prior to the detection of the apoptotic index. After staining, the percentages of live and dead cells were analyzed on NovoCyte flow cytometry (Agilent Technologies, USA).

Cell Culture with C-Vx

PBMCs adjusted to $1\times10^6$ cells/mL were cultured for 72 hours at 37° C. with/without the addition of C-Vx (Hamida Pharma-USA & Miracle Labs-Turkey) at a concentration of 1/250 determined by dose experiments performed in our laboratory. Following cell culture, PBMCs were used for intracellular cytokine measurement and cytotoxicity assay.

Intracellular Cytokine Measurement

In order to measure the intracellular cytokine levels of T lymphocytes, cultured PBMCs ($1\times10^6$ cells/mL) for 72 hours at the presence or absence of 1/250 C-Vx were stimulated with Cell Stimulation Cocktail with Brefeldin A (Biolegend, San Diego, USA) and additionally cultured for 4 hours at 370 C incubator. After the cell culture, PBMCs were washed with PBS and supernatants were discarded. Prior to the detection of intracellular cytokine levels, cell surface staining was performed using anti-human-CD3 BV785, -CD4 PE and -CD8 FITC monoclonal antibodies (mAbs) (all from Biolegend, San Diego, USA). Stained-PBMCs were washed after the incubation for 20 minutes, and for intracellular staining, Fixation/Permeabilization Kit (BD Cytofix/Cytoperm, California, USA) was used according to the manufacturer's protocol. Simply, cells were fixed and then permeabilized together with adding of anti-IFN-γ PE/Cy7, -TNF-α APC/Cy7, -IL-4 APC, -IL-10 BV421, -IL-17 Alexa Fluor 700 mAbs. After washing, samples were measured and analyzed on a NovoCyte flow cytometry running NovoExpress software (ACEA Biosciences, USA).

Cell Proliferation Assay by CFSE

To evaluate the proliferative responses of cells to C-Vx substance, Carboxyfluorescein succinimidyl ester (CFSE) dilution method was used which based on labeling cells with CFSE and evaluating the fluorescence halved by each cell division. PBMCs (up to $2\times10^7$) suspended in RPMI-1640 medium (Gibco, Paisley, UK) were stained with 1 μl of 5 mM CFSE solution (Thermo Fisher Scientific, USA) and incubated for 6 minutes at 40 C. After washing with PBS, PBMCs were cultured for 120 hours at 370 C in 5% $CO_2$ environment with the absence or existence of 1/250 C-Vx (Hamida Pharma-USA & Miracle Labs-Turkey) together with/without 5 μl/ml phytohaemagglutinin (PHA, Thermo Fisher, USA) addition. Following cell culture, the supernatants of each condition were collected and stored at −200° C. for future analysis. PBMCs were taken from the respective wells (US: unstimulated, PHA: phytohemagglutinin-stimulated, C-Vx and PHA+C-Vx) into separate tubes for cell surface staining with anti-human-CD3 BV785, -CD4 PE-Cy7, -CD8 APC-Cy7, -CD16 BV570 and anti-CD56 BV711 (all from Biolegend, USA) mAbs and incubated. Stained cells were washed following incubation and analyzed in a Novocyte flow cytometry running NovoExpress software (ACEA Biosciences, USA).

Cytotoxic Activity of NK Cells

PBMCs ($1 \times 10^6$ cells/mL) cultured for 72 hours with/without 1/250 C-Vx (Hamida Pharma-USA & Miracle Labs-Turkey) addition were washed twice with PBS after cell culture. Cells ($5 \times 10^5$) were stained with anti-human CD107a APC mAb (Biolegend, San Jose, Calif., USA) and cultured alone or together with K562 cells ($4 \times 10^4$) at an 10:1 effector/target (E:T) ratio for 5 hours at 37° C. incubator. After the incubation, PBMCs were labeled with anti-human-CD56 BV711, -CD16 BV570, -CD3 BV785 and -CD8 FITC (Biolegend, San Jose, Calif., USA) mAbs. Samples were fixed and permeabilized according to the manufacturer's directions (Cytofix&Cytoperm Kit, BD Biosciences, San Jose, Calif., USA), and then stained with anti-human-Perforin PerCp/Cy5.5 and -Granzyme B Alexa Fluor 700 (Biolegend, San Jose, Calif., USA) mAbs. Stained cells were measured and analyzed by NovoCyte flow cytometry running NovoExpress software (ACEA Biosciences, USA).

RNA Isolation and cDNA Synthesis

After the incubation times, RNA isolations of experimental groups were performed using RNAeasy® Micro Kit following the manufacturer's instructions. Total RNA was converted into cDNA with a reverse transcription method using the QuantiTect® Reverse Transcription Kit, which was used to determine the expression ratio of the target gene via qRT-PCR.

Quantitative Real-Time PCR Analysis

Quantitative real-time PCR analyses were performed using StepOne & StepOnePlus Real-Time PCR Systems (Applied Biosystems, USA). The gene expression analyses of IRF3 (Hs01547283_m1) and ACTR1B (as control, Hs00194899_m1) were done utilizing TaqMan Universal Master Mix (2×) and TaqMan Gene Expression Assay Mix (40×) (Applied Biosystems, USA). Relative gene expression of IRF3 was calculated by $2^{-\Delta\Delta CT}$, relative to the ACTR1B.

Measurement of Bradykinin, IRF-3 and IFN-α Levels by ELISA

All plasma and culture supernatants collected and stored at −80° C. were thawed. The levels of Bradykinin (AFG Bioscience, Cat No. EK700040), IRF-3 (AFG Bioscience, Cat No. EK710036) and IFN-α (AFG Bioscience, Cat No. EK710029) were measured by ELISA according to the manufacturer's instructions. Optical densities were measured at 450 nm and concentrations were calculated by reference to the standard curves.

Cytokine Measurement by Multiplex

The cytokine levels in plasma and culture supernatants were detected by multiplex assay kit (LEGENDplex, Biolegend, USA) which is a bead-based immunoassay provides quantification of multiple soluble analytes simultaneously in biological samples using a flow cytometer. By this method, cytokines including IL-1β, IL-2, IL-4, IL-5, IL-6, IL-8, IL-10, IL-12p70, IL-13, GM-CSF, TNF-α and IFN-γ were measured according to the manufacturer's protocol. Acquisition of samples were performed with NovoCyte flow cytometry running NovoExpress software (ACEA Biosciences, USA). The assay sensitivity is presented in Table 3.

TABLE 3

Multiplex assay sensitivity

| Analyte (pg/mL) | Sensitivity in Serum (pg/mL) | Sensitivity in Cell Culture Medium (pg/mL) |
|---|---|---|
| hIL-1β | 1.5 + 0.6 | 1.7 + 0.5 |
| hIFN-γ | 1.3 + 1.0 | 1.5 + 1.2 |
| hTNF-α | 0.9 + 0.8 | 1.6 + 0.1 |
| hIL-6 | 1.5 + 0.7 | 1.5 + 0.3 |
| hIL-8 | 2.0 + 0.5 | 1.8 + 0.7 |
| hIL-12p70 | 2.0 + 0.2 | 2.0 + 0.1 |
| hIL-5 | 1.2 + 1.3 | 1.3 + 1.2 |
| hIL-4 | 1.0 + 0.8 | 0.9 + 0.8 |
| hIL-13 | 1.4 + 0.7 | 1.4 + 0.5 |
| hIL-10 | 0.7 + 0.4 | 0.9 + 0.4 |
| hIL-2 | 1.4 + 0.4 | 1.4 + 0.5 |
| hGM-CSF | 0.92 ± 0.45 | 1.15 ± 0.36 |

Statistical Analysis

Statistical analyses were performed with SPSS 21.0 software (SPSS Inc., Chicago, Ill., USA). Distribution normality of donor groups was analyzed by Shapiro-Wilk test. The before/after groups which were found to be normally distributed were analyzed with parametric Paired-T Test, Wilcoxon test was used for non-parametric values. One-way ANOVA was used in order to compare donor groups with each other, and post-hoc evaluations were performed by Tukey's test. The values of ($p<0.05$) were accepted as the statistically significant. Graphs were created using Graphpad Prism 9.0 Software. Data were presented as mean±standard error mean (SEM).

Results

The Effects of C-Vx on the Levels of T and NK Cells

Figure 1B:
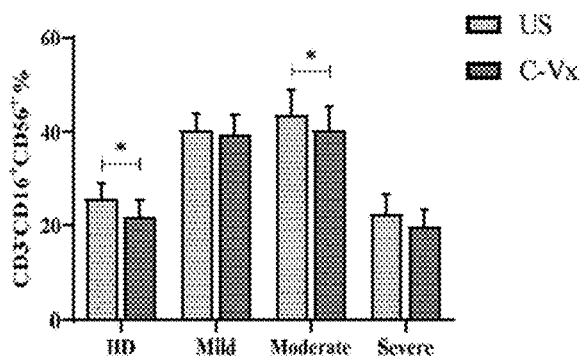
Figure 1C:
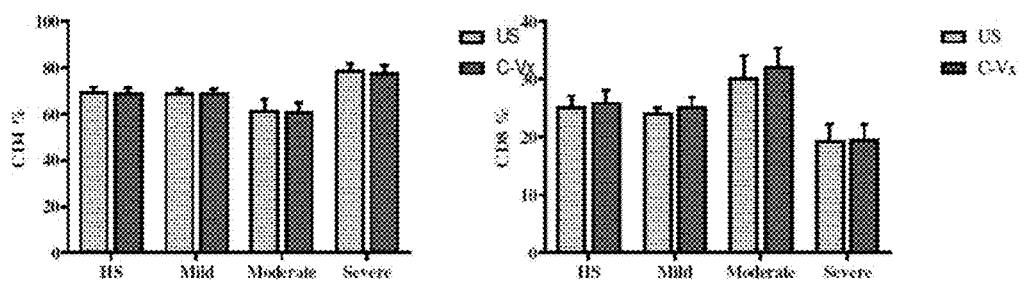

Prior to the functional assays, the effects of C-Vx on $CD4^+$ and $CD8^+$ T cell frequencies was explored in patient groups and healthy donors. The concentration of C-Vx used in cell culture was determined by dose experiments giving the optimum result at 1/250 (data not shown). CD3+ total T cell frequencies of mild and moderate patients as well as healthy donors was significantly decreased upon 1/250 C-Vx addition in comparison with unstimulated condition (p=0.022, p=0.023, p=0.008, respectively). However, there was no significant difference in $CD4^+$ and $CD8^+$ T cell ratios of all donor groups between the conditions with or without C-Vx addition. A similar decreasing effect of C-Vx stimulation those on $CD3^+$ T cell levels was also observed on $CD3^-CD16^+CD56^+$ NK cell levels. The frequencies of NK cells were significantly reduced by C-Vx in moderate patients and healthy donors (p=0.034, p=0.014, respectively) (FIG. 1).

C-Vx-Induced Anti-Inflammatory Cytokine Secretion of T Cells

In order to evaluate the effects of C-Vx on T cell functions of COVID-19 patients, primarily, intracellular levels of IFN-γ, IL-17, TNF-α, IL-4 and IL-10 in $CD4^+$ and $CD8^+$ T cells in response to C-Vx addition were measured after cell culture.

Figure 2:
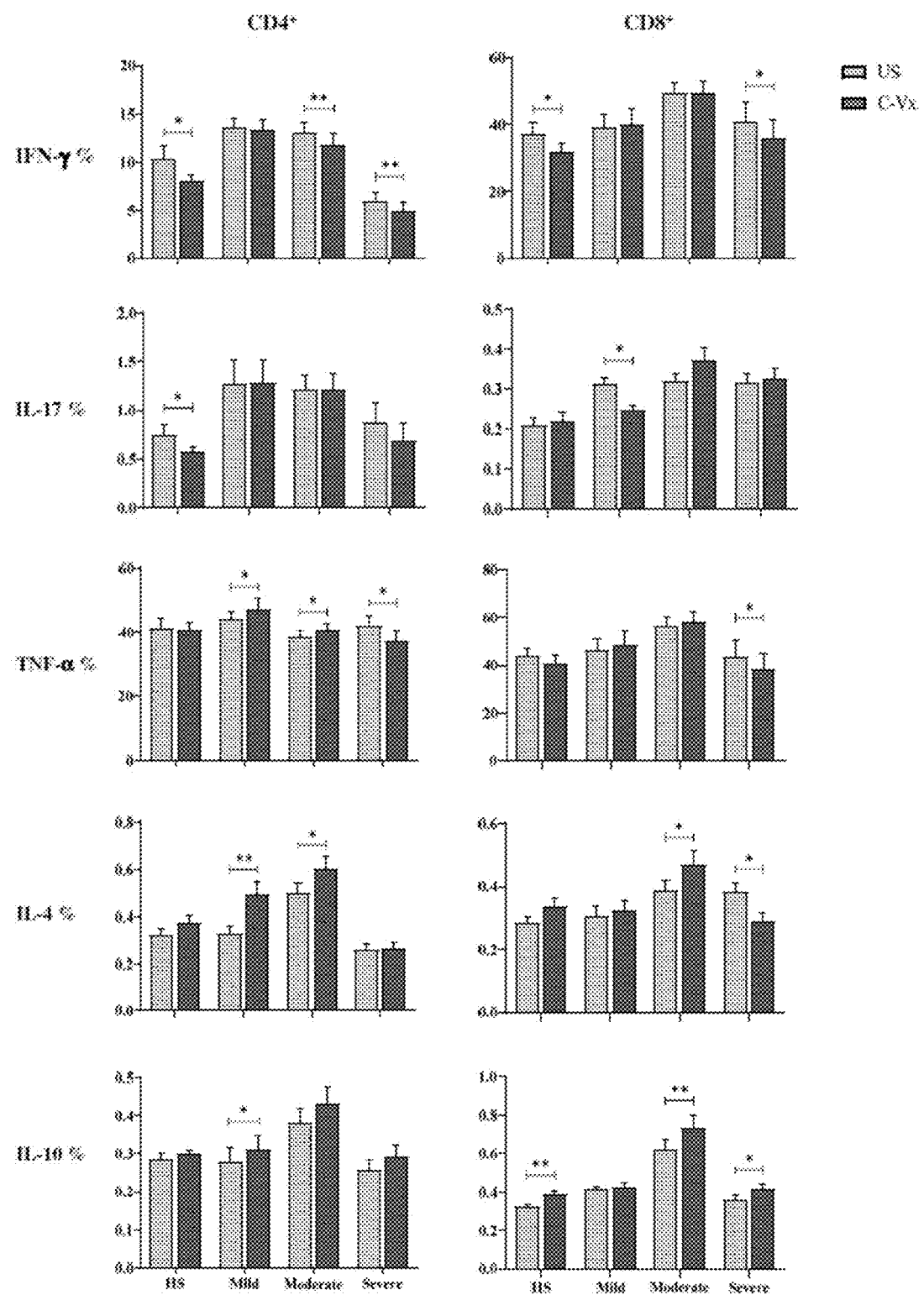
FIG. 2 provides graphs showing the levels of intracellular cytokines of CD4$^+$ and CD8$^+$ T cell subsets with/without C-Vx.

IFN-γ levels of $CD4^+$ T cells were significantly reduced by C-Vx addition in moderate and severe patients as well as healthy donors (p=0.008, p=0.003, p=0.026, respectively) (FIG. 2). Similarly, IL-17 levels of CD4+ T cells were decreased upon C-Vx addition in severe patients and healthy donors (p=0.01) although no significance was found in severe patients. The levels of TNF-α, another proinflammatory cytokine, were significantly increased following C-Vx stimulation in mild and moderate patients whereas decreased in severe patients while not altered in healthy donors (p=0.029, p=0.036, p=0.033, respectively). On the other hand, the stimulation with C-Vx was seemed to increase the levels of IL-4 and IL-10, which are named as Th2-type cytokines, in $CD4^+$ T cells. IL-4 content of $CD4^+$ T cells were significantly elevated by C-Vx addition in mild and moderate patients (p=0.001, p=0.013, respectively). C-Vx addition led to increase IL-10 levels of $CD4^+$ T cells in all patient groups although there was significance only in mild patients (p=0.025).

A similar effect of C-Vx on IFN-γ levels of $CD4^+$ T cells was also observed on $CD8^+$ T cells. IFN-γ+$CD8^+$ T cell frequencies of severe patients and healthy donors were significantly reduced by C-Vx addition (p=0.029, p=0.023, respectively) (FIG. 2). IL-17 levels of $CD8^+$ T cells were as well decreased after C-Vx stimulation in mild patients (p=0.010). Similar to $CD4^+$ T cells, TNF-α content of $CD8^+$ T cells in severe patients was also found to be decreased by C-Vx addition (p=0.02). Interestingly, C-Vx stimulation significantly increased IL-4 levels of $CD8^+$ T cells in moderate patients (p=0.014) whereas reducing it in severe patients (p=0.02). Similar to $CD4^+$ T cells, $CD8^+$ T cells also had significantly higher levels of IL-10 following C-Vx addition in moderate and severe patients as well as healthy donors (p=0.009, p=0.02, p=0.002, respectively).

Lymphocyte Proliferation Induced by C-Vx

The proliferative responses of lymphocytes of donor groups in response to C-Vx stimulation were investigated by CFSE dilution method, which permits proliferation analysis of lymphocyte subsets. PHA was used as a positive control and the role of C-Vx on both spontaneous and also PHA-induced proliferation was assayed. The obtained data of $CD3^+$, $CD4^+$ and $CD8^+$ T cells as well as $CD3^-CD16^+CD56^+$ NK cells were evaluated as % proliferation.

Figure 3:
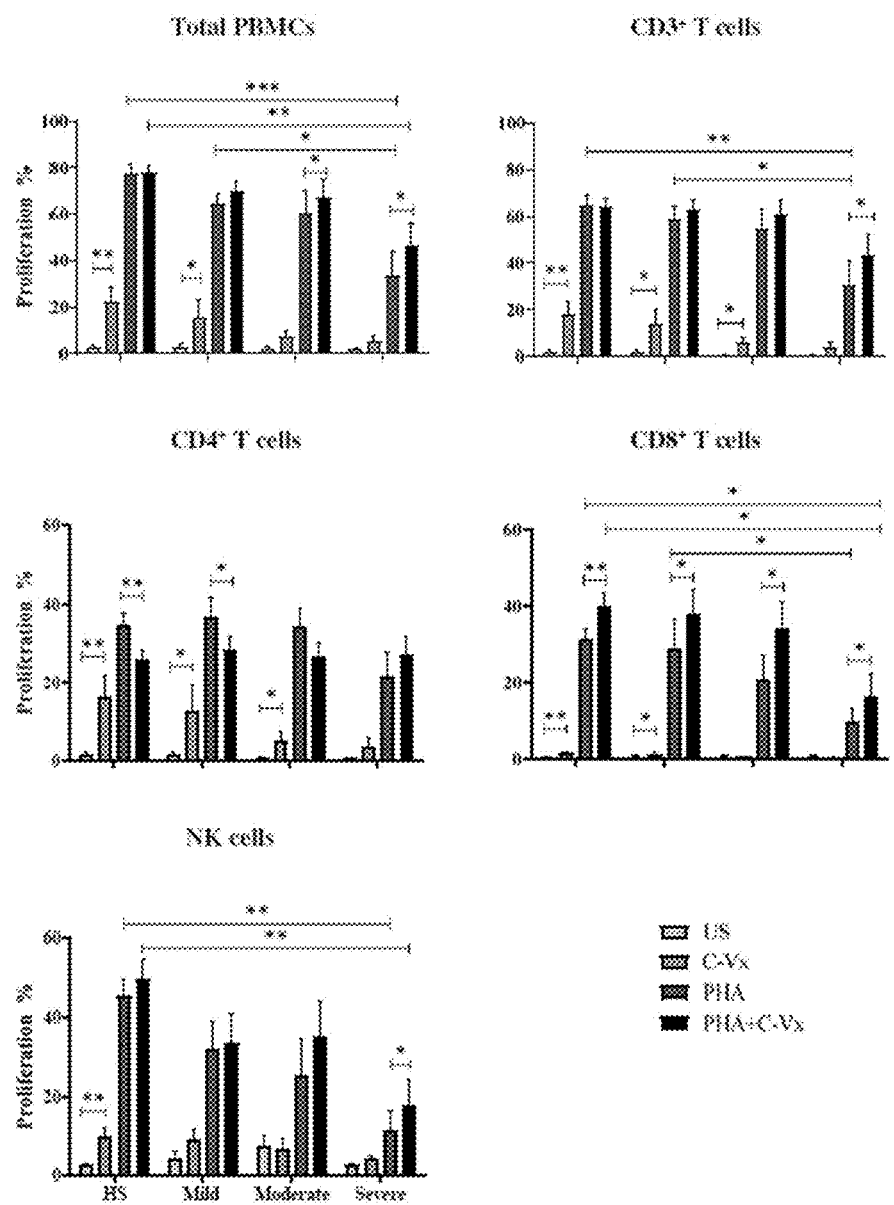
FIG. 3 provides graphs showing the proliferative responses of T and NK cells following stimulation with C-Vx.

When proliferation of total PBMCs was investigated, presence of C-Vx alone induced significant proliferation in mild patients besides healthy donors (p=0.036 and p=0.005, respectively) (FIG. 3). This effect was the strongest in healthy donors and was declining with the increased severity of the disease. PHA induced strong proliferation especially in healthy donors as expected, however severe patients had significantly diminished proliferation in comparison with healthy donors and mild patients (p=0.001 and p=0.029, respectively). The co-existence of C-Vx and PHA triggered elevated PBMC proliferation levels comparable with PHA alone in all patient groups. Notably, diminished PHA-induced proliferation with increased severity of the disease was regained with co-existence of C-Vx. In severe and also moderate patients, addition of C-Vx together with PHA triggered significantly stronger proliferation in comparison with the presence of PHA alone (p=0.021 and p=0.043, respectively). However, the elevated proliferative responses observed in severe patients' response to combined stimulation of C-Vx and PHA was significantly lower than that in healthy donors (p=0.005).

Investigation of $CD3^+$ T cell proliferation revealed similar properties with PBMCs. Briefly, C-Vx significantly induced the proliferation of $CD3^+$ T cells in mild, moderate, severe patients as well as healthy donors (p=0.012, p=0.028, p=0.028 and p=0.007, respectively). The proliferative capabilities of $CD3^+$ T cells in response to C-Vx stimulation were observed to decline in concordance with increased disease severity, similar to the case of PHA-induced proliferation. PHA-induced proliferation in severe patients was significantly lower than that of healthy donors (p=0.007) which was potentiated with the existence of C-Vx (p=0.038). PHA-induced proliferation of severe patients was significantly diminished in comparison with that of mild patients (p=0.045).

$CD4^+$ T cells responded to C-Vx alone and proliferated consequently in mild and moderate patients, and in healthy donors (p=0.012, p=0.018 and p=0.005, respectively). No significant difference in PHA-induced proliferation among healthy donors and patient groups was observed, but proliferation in response to combination of C-Vx and PHA was found to limit PHA-induced proliferation in healthy donors and in mild patients (p=0.005 and p=0.012, respectively). In severely ill patients, C-Vx in addition to PHA was observed to trigger stronger proliferation in comparison with presence of PHA alone, though without statistical significance.

When $CD8^+$ T cell proliferation was investigated, C-Vx alone was found to induce $CD8^+$ T cell proliferation in healthy donors as well as in mild patients (p=0.008 and p=0.018, respectively). Proliferation in response to both PHA and combination of PHA with C-Vx was found to decline with the increased disease severity. PHA induced proliferation in severe patients were significantly reduced in comparison with healthy donors (p=0.015). On the other hand, addition of C-Vx to PHA significantly up-regulated the proliferation levels in mild, moderate and severe patients as well as in healthy donors (p=0.017, p=0.018, p=0.011 and p=0.013, respectively). However, the proliferative responses against combination of C-Vx and PHA in severe patients was significantly diminished in comparison with that of healthy subjects (p=0.019).

$CD3^-CD16^+CD56^+$ NK cell proliferation in response to C-Vx was significantly increased in response to C-Vx alone only in healthy donors (p=0.005). The proliferation levels at PHA-induced conditions tended to decrease with increased disease severity, while it was significantly diminished in severe patients, in comparison with healthy donors (p=0.002). Combination of PHA and C-Vx had an up-regulatory effect in comparison with PHA alone, which had significance only in severe patients (p=0.038). However, the combination of PHA and C-Vx in severe patients was not able to up-regulate the proliferation to the levels of healthy donors, which was significantly high (p=0.002).

Figure 4:
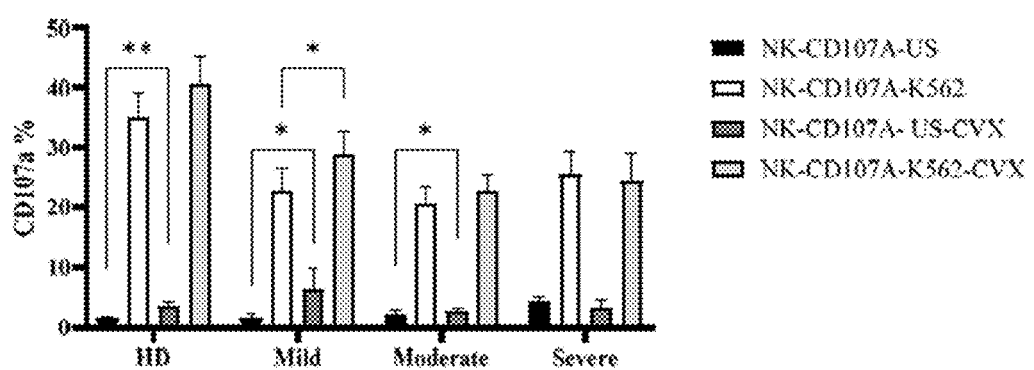
FIG. 4 provides graphs showing the measurement of NK cell cytotoxicity depending on CD107a degranulation. The levels of CD107a+ NK cells were detected using K562 cells at 10:1 E:T ratio in complete medium in the absence or presence of C-Vx, in peripheral blood of patients infected with SARS-CoV-2 and healthy donors.

The Cytotoxicity Analysis Depending on CD107a, Perforin and Granzyme B Expression The cytotoxicity of NK and $CD8^+$ T cells were shown to have an exhausted phenotype in patients with COVID-19 Varchetta et al., Cellular and Molecular Immunology, 18: 604-612 (2021). To investigate the effect of C-Vx on the cytotoxic potential of NK and $CD8^+$ T cells, we performed the cytotoxicity assay depends on measuring the levels of CD107a, Perforin and Granzyme B, which are directly related with cytotoxic activity. No significant difference was found for Perforin and Granzyme B expressions of $CD3^-CD16^+CD56^+$ NK and $CD8^+$ T cells in response to C-Vx among patient groups and healthy donors (p>0.05). When the effectiveness of C-Vx stimulation was evaluated for CD107a levels of NK cells, it was determined to be significantly up-regulated in both healthy donors and patient groups except in severe cases. In conditions without K562 stimulation, CD107a levels of NK cells were significantly increased upon C-Vx addition in mild and moderate patients as well as healthy donors (p=0.013, p=0.037, p=0.007, respectively) (FIG. 4). In presence of K562, C-Vx addition resulted a significant elevation only in mild patients (p=0.013). In all donor groups, CD107a expression levels of CD8+ T cells were increased with no statistical significance, in response to K-562 co-culture, regardless of C-Vx stimulation.

IRF3 Gene Expression on PBMCs Stimulated with C-Vx

Figure 5A:
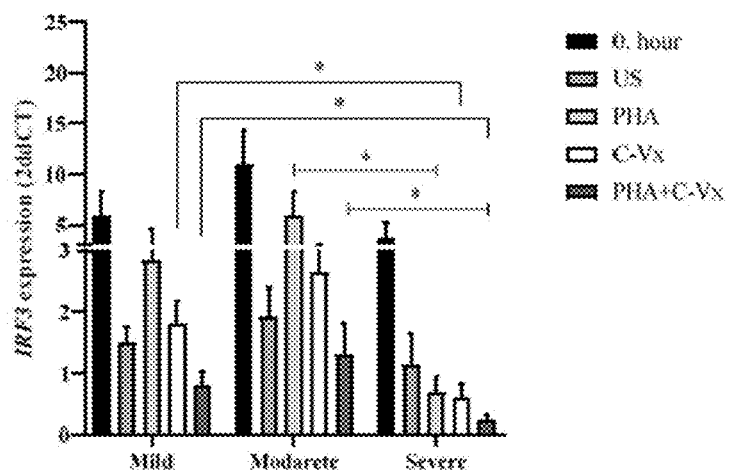
FIGS. 5A and 5B provide graphs showing (A) IRF3 gene expression of COVID-19 patients and (B) Bradykinin, IRF-3 and IFN-α levels in plasma samples and supernatants after 120 h cell culture at the presence/absence of C-Vx.
Figure 5B:
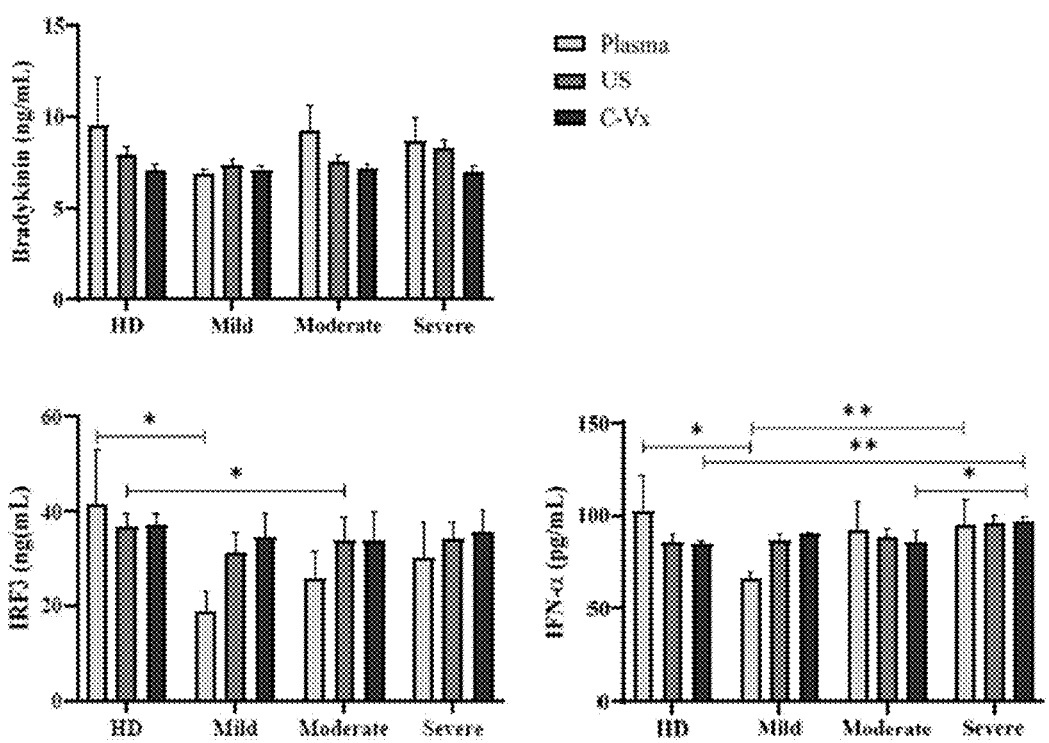

In order to evaluate the effect of C-Vx on IRF3 gene expression, PBMCs were stimulated with C-Vx and cultured for 72 hours. As a result of the stimulation, an evaluation was made according to healthy donors. Accordingly, it was determined that PHA alone and additionally C-Vx to the culture medium caused an increase in IRF3 expression in moderate cases compared to severe cases ($p=0.019$ and $p=0.01$, respectively) (FIG. 5). It was determined that C-Vx alone increased IRF3 expression in mild and moderate cases compared to severely ill cases ($p=0.048$ and $p=0.012$, respectively). These results were interpreted as C-Vx had a significant effect on mild and moderately ill cases.

Determination of Bradykinin, IRF-3 and IFN-α in Plasma and Supernatant

Figure 6A:
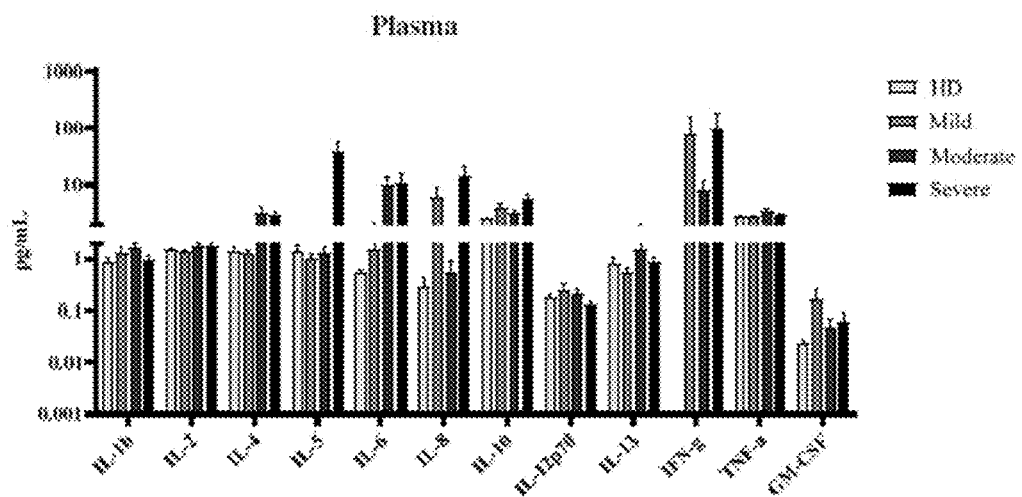
FIGS. 6A and 6B provide graphs showing the cytokine levels of healthy donors (HD) and patient groups measured by multiplex in A) plasma samples and B) culture supernatants of PBMCs cultured for 120 h with/without C-Vx addition.
Figure 6B:
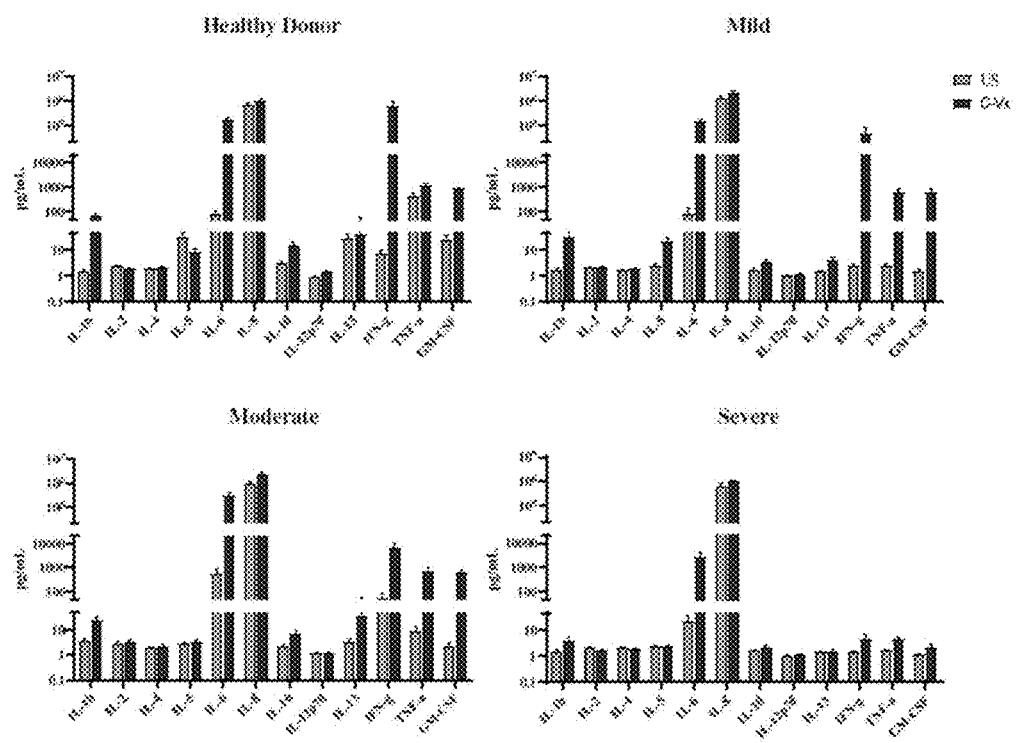

When the levels of Bradykinin, IRF-3 and IFN-α measured in plasma were evaluated between the groups using ELISA method, no difference was found in Bradykinin levels between the groups. While the level of IFN-α was lower in mild form of the disease compared to severe patients and healthy donors ($p=0.007$, $p=0.035$, respectively) (FIG. 5). After the stimulation with C-Vx, IFN-α levels in the supernatant were found to be higher in severe patients compared to healthy donors and moderate patients ($p=0.009$ and $p=0.017$, respectively). According to the results, it is seen that the level of IFN-α, which is low in the plasma in mild cases, tends to increase after stimulation with C-Vx. The measurement of the effects of C-Vx on cytokine secretion by multiplex is shown in FIG. 6.

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A composition comprising:
   attenuated Measles virus;
   attenuated Mumps virus;
   attenuated Rubella II virus;
   scorpion antivenom; and
   a pharmaceutically acceptable carrier.

2. The composition of claim 1, further comprising one or more nutrients selected from the group consisting of glutathione, zinc, and vitamin D.

3. The composition of claim 1, wherein the attenuated Measles virus provide a CCID50 from 200 to 300, the attenuated Mumps virus particles provide a CCID50 from 5500 to 6000, and the attenuated Rubella II virus particles provide a CCID50 from 200 to 300.

4. The composition of claim 1, wherein the amount of scorpion antivenom provides an LD50 of from 3 to 5.

5. The composition of claim 1, wherein the pharmaceutically acceptable carrier is a carrier suitable for administration by injection.

* * * * *